(12) United States Patent
Coolbaugh et al.

(10) Patent No.: US 11,912,741 B2
(45) Date of Patent: Feb. 27, 2024

(54) CONTINUOUS PRODUCTION OF RECOMBINANT PROTEINS

(71) Applicant: Genzyme Corporation, Cambridge, MA (US)

(72) Inventors: Michael Coolbaugh, Waltham, MA (US); Tarl Vetter, Framingham, MA (US); Chad Varner, Marlborough, MA (US); Kevin Brower, Holliston, MA (US)

(73) Assignee: GENZYME CORPORATION, Cambridge, MA (US)

( * ) Notice: Subject to any disclaimer, the term of this patent is extended or adjusted under 35 U.S.C. 154(b) by 585 days.

(21) Appl. No.: 16/837,126

(22) Filed: Apr. 1, 2020

(65) Prior Publication Data

US 2020/0317728 A1    Oct. 8, 2020

Related U.S. Application Data

(60) Provisional application No. 62/828,755, filed on Apr. 3, 2019.

(51) Int. Cl.
| | |
|---|---|
| *C07K 1/36* | (2006.01) |
| *C12M 1/26* | (2006.01) |
| *C12M 1/12* | (2006.01) |

(52) U.S. Cl.
CPC .............. *C07K 1/36* (2013.01); *C12M 33/14* (2013.01); *C12M 37/02* (2013.01)

(58) Field of Classification Search
CPC ............ B01D 15/1807; B01D 15/1864; B01D 2311/26; B01D 2311/2688;
(Continued)

(56) References Cited

U.S. PATENT DOCUMENTS

| | | | |
|---|---|---|---|
| 2014/0255994 A1* | 9/2014 | Konstantinov | .... B01D 15/1864 435/69.6 |
| 2015/0299249 A1* | 10/2015 | Herigstad | ................ C07K 1/22 530/416 |

(Continued)

FOREIGN PATENT DOCUMENTS

| | | |
|---|---|---|
| EP | 2649016 A2 | 10/2013 |
| WO | 2003043439 A1 | 5/2003 |

(Continued)

OTHER PUBLICATIONS

Bisschops et al., "6. Two Mutually Enabling Trends: Continuous Bioprocessing and Single-Use Technologies"; in: Ganapathy Subramanian: "Continuous Biomanufacturing: Innovative Technologies and Methods", Wiley-VHC, Wenheim, XP009521341, ISBN: 978-3-527-34063-7, pp. 149-169, (2018).

(Continued)

*Primary Examiner* — Jennifer Wecker

(74) *Attorney, Agent, or Firm* — McDonnell Boehnen Hulbert & Berghoff LLP

(57) ABSTRACT

The present disclosure relates to methods and systems for the continuous production of recombinant proteins. In particular embodiments, the disclosure relates to methods and systems using capture chromatography, post-capture chromatography, virus filtration, and ultrafiltration/diafiltration for the continuous production of recombinant proteins.

24 Claims, 23 Drawing Sheets

(58) Field of Classification Search
CPC ............ B01D 2315/08; B01D 2315/16; B01D 61/14; B01D 61/145; B01D 61/58; C07K 1/22; C07K 1/34; C07K 1/36; C07K 16/00; C12M 33/14; C12M 37/02; C12M 47/10; C12P 21/005
See application file for complete search history.

(56) References Cited

U.S. PATENT DOCUMENTS

| | | | | |
|---|---|---|---|---|
| 2015/0345689 | A1* | 12/2015 | Selker | B01D 35/28 422/534 |
| 2017/0058308 | A1* | 3/2017 | Aakesson | B01D 15/3804 |
| 2018/0051054 | A1* | 2/2018 | Vetter | C07K 16/00 |

FOREIGN PATENT DOCUMENTS

| | | | | |
|---|---|---|---|---|
| WO | 2014/180852 | A1 | 11/2014 | |
| WO | 2015/175679 | A2 | 11/2015 | |
| WO | WO-2015175679 | A2 * | 11/2015 | ............ B01D 61/142 |
| WO | WO-2015198320 | A1 * | 12/2015 | ............. C07K 1/165 |
| WO | WO2018/035116 | | 2/2018 | |
| WO | WO-2018164995 | A1 * | 9/2018 | ............ A61K 38/465 |

OTHER PUBLICATIONS

Godawat et al., "End-to-end integrated fully continuous production of recombinant monoclonal antibodies", Journal of Biotechnology, 213:13-9, (Nov. 2015).
Konstantinov et al., "White Paper on Continuous Bioprocessing" J. Pharm. Sci. 104(3): 813-20 (Mar. 2015).
Orozco et al., "Design, construction, and optimization of a novel, modular, and scalable incubation chamber for continuous viral inactivation", Biotechnology Progress, 33(4): 954-965, (Jul. 2017).
Parker et al., "Design of a novel continuous flow reactor for low pH viral inactivation", Biotechnology and Bioengineering, 115(3): 606-616, (Mar. 2018).
Steinebach et al., "Design and operation of a continuous integrated monoclonal antibody production process", Biotechnology Press, 33(5): 1303-1313, (Sep. 2017).
Zydney, "Continuous downstream processing for high value biological products: A Review" Biotechnol. Bioeng. 113(3): 465-75 (Mar. 2016).
The International Search Report and Written Opinion of the International Searching Authority for International Application No. PCT/US2020/026107; dated Jul. 10, 2020, p. 1-6.
Gracheva. "Technology of Enzyme Preparations". 2nd edition, 1987 in "Textbooks and tutorials for Higher Educational Institutions Students". (Machine translation provided).

* cited by examiner

CONTINUOUS PRODUCTION OF RECOMBINANT PROTEINS

This application claims the benefit of U.S. Provisional Application No. 62/828,755, filed Apr. 3, 2019 the disclosure of which is explicitly incorporated by reference herein.

FIELD OF THE DISCLOSURE

The present disclosure relates to methods and systems for the continuous production of recombinant proteins. In particular embodiments, the disclosure relates to methods and systems using capture chromatography, post-capture chromatography, virus filtration, and ultrafiltration/diafiltration for the continuous production of recombinant proteins.

BACKGROUND

Continuous manufacturing is a routine way of production for industries such as petrochemical and food production. Benefits of a continuous process include steady state operation, reduced equipment size, high-volumetric productivity, streamlined process flow, low-cycle times, and reduced capital cost. Konstantinov et al., *J. Pharm. Sci.* 104(3): 813-20 (2015).

Continuous manufacturing has not been widely implemented in the biopharmaceutical industry. Because technological needs for upstream and downstream development are rather different, the experience with continuous downstream operations is limited. Thus, there remains a need for integrated continuous bioprocesses that can be run for extended periods of time with minimal operator interaction for the biopharmaceutical industry.

SUMMARY

Provided herein is a continuous method for producing a recombinant protein, the method comprising: (a) capturing the recombinant protein from a substantially cell-free sample using one or a plurality of capture chromatography systems and eluting the recombinant protein from the one or plurality of capture chromatography systems to produce eluates comprising the recombinant protein, wherein a single or multiple eluates are homogenized into a single mixture comprising the recombinant protein, (b) subjecting the single mixture to one or a plurality of post-capture chromatography systems and collecting product output comprising the recombinant protein, and (c) subjecting the product output to ultrafiltration and diafiltration to purify the recombinant protein, wherein the method is integrated and continuous from step (a) to step (c).

Also provided herein is a manufacturing system for producing a recombinant protein, the manufacturing system comprising: (a) a first unit operation comprising a bioreactor comprising host cells that produce the recombinant protein, (b) a second unit operation comprising one or a plurality of capture chromatography systems, (c) a third unit operation comprising one or a plurality of post-capture chromatography systems, and (d) a fourth unit operation comprising an ultrafiltration system and diafiltration system.

Also provided herein is a continuous method for producing a recombinant protein, the method comprising: (a) capturing the recombinant protein from a substantially cell-free sample using one or a plurality of capture chromatography systems and eluting the recombinant protein from the one or plurality of capture chromatography systems to produce eluates comprising the recombinant protein, wherein the eluates are homogenized into a single mixture comprising the recombinant protein, (b) subjecting the homogenized single mixture to virus inactivation, (c) subjecting the homogenized single mixture from step (b) to one or a plurality of post-capture chromatography systems and collecting product output comprising the recombinant protein, (d) subjecting the product output of step to virus filtration, and (e) subjecting the product output from step (d) to ultrafiltration and diafiltration to purify the recombinant protein, wherein the method is integrated and continuous from step (a) to step (e).

Other aspects, embodiments, and implementations will become apparent from the following detailed description and claims, with reference, where appropriate, to the accompanying drawings.

BRIEF DESCRIPTION OF THE DRAWINGS

FIG. 2A shows the unit operation integration durations for continuous operation for each operation unit. FIG. 2B shows the average protein residence time for each unit operation. The methods and systems disclosed herein generated ~5 kg drug substance over a 25-day period.

FIG. 3A shows Protein A eluate concentrations (g/L), FIG. 3B shows Protein A eluate residual host cell proteins, FIG. 3C shows Protein A eluate residual Protein, FIG. 3D shows Protein A inlet mass flow, and FIGS. 3E and 3F show Protein A ultraviolet chromatogram.

FIG. 4A shows the viral inactivation pH maintained throughout the unit operation, FIG. 4B shows protein concentration prior to inactivation, FIG. 4C shows protein mass flow during viral inactivation, FIG. 4D shows acid flow during viral inactivation, FIG. 4E shows base flow during viral inactivation, FIG. 4F shows high molecular weight species during viral inactivation, and FIG. 4G shows protein concentration following viral inactivation.

FIG. 5A shows post-capture eluate residual Protein A, FIG. 5B shows post-capture eluate protein concentration, FIG. 5C shows ultraviolet chromatogram, and FIG. 5D show post-capture eluate residual host cell protein.

FIG. 6B shows protein concentration following viral filtration, FIG. 6C shows high molecular weight species following viral filtration, FIG. 6D shows protein mass flux during viral filtration, FIG. 6E shows filtrate volume flux during virus filtration, FIG. 6F shows transmembrane pressure during viral filtration, and FIG. 6G shows filter performance during viral filtration.

FIG. 7A shows protein concentration and conversion following ultrafiltration, FIG. 7B shows filter performance during ultrafiltration, FIG. 7C shows inlet protein mass flux during ultrafiltration, FIG. 7D shows permeate volume flux during ultrafiltration, and FIG. 7E shows transmembrane pressure during ultrafiltration.

FIG. 8A shows permeate volume flux during diafiltration, FIG. 8B shows protein mass flux during diafiltration, FIG. 8C shows transmembrane pressure during diafiltration, FIG. 8D shows diafiltration ratio, and FIG. 8E shows filter performance during diafiltration.

FIG. 9A shows the concertation of the drug substance, FIG. 9B shows high molecular weight species of the drug substance, FIG. 9C shows the charge profile of the drug substance, FIG. 9D shows the osmolality of the drug substance, FIG. 9E shows the pH of the drug substance, FIG. 9F shows host cell protein as measured by ELISA for the drug substance, FIG. 9G shows the non-reduced purity of the drug substance, and FIG. 9H shows the residual Protein A of the drug substance.

DETAILED DESCRIPTION

Figure 1:
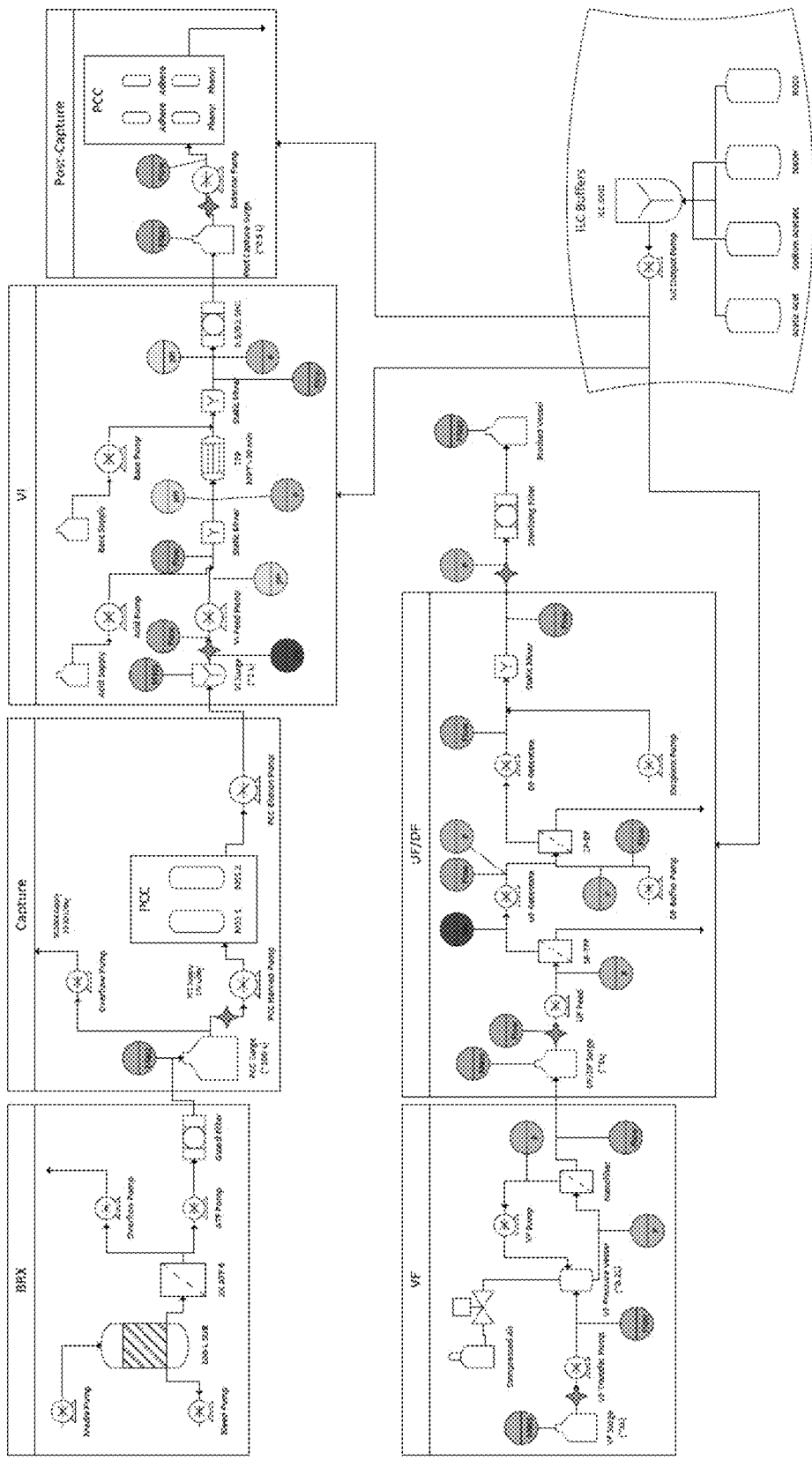
FIG. 1 is a schematic illustrating the process flow of the methods disclosed herein. The process flow includes a continuous process for production of a recombinant protein using in-line buffers comprising: (1) production of the recombinant protein in a bioreactor coupled with dual Alternating Tangential Flow (ATF) filters and cell separation (labeled as "BRX"), (2) capture of the recombinant protein using one or plurality of capture chromatography systems to capture the recombinant protein present in the culture medium obtained from the bioreactor connected to the capture chromatography system (labeled as "Capture"), (3) viral inactivation of the medium (labeled as "VI"), (4) subjecting the medium to one or a plurality of post-capture chromatography systems (labeled as "Post-Capture"), (5) viral filtration of the medium, and (6) ultrafiltration/diafiltration of the medium.
Figure 2B:
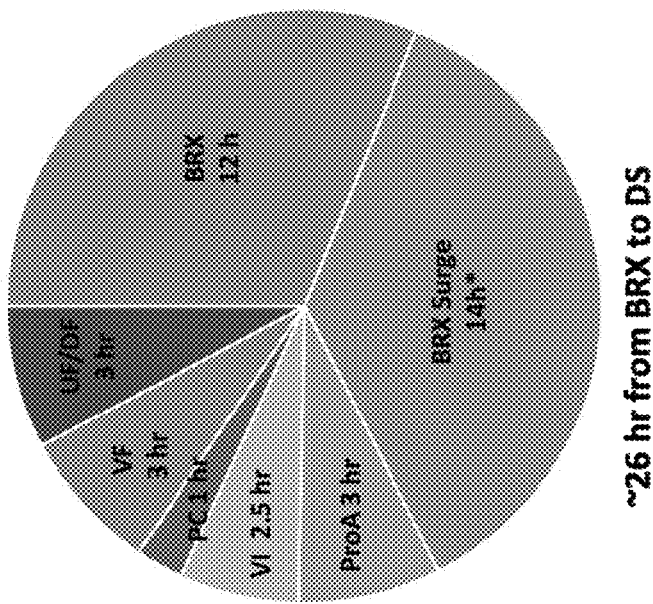
FIGS. 2A and 2B show an overview of the unit operation integration of the methods and systems disclosed herein.
Figure 2A:
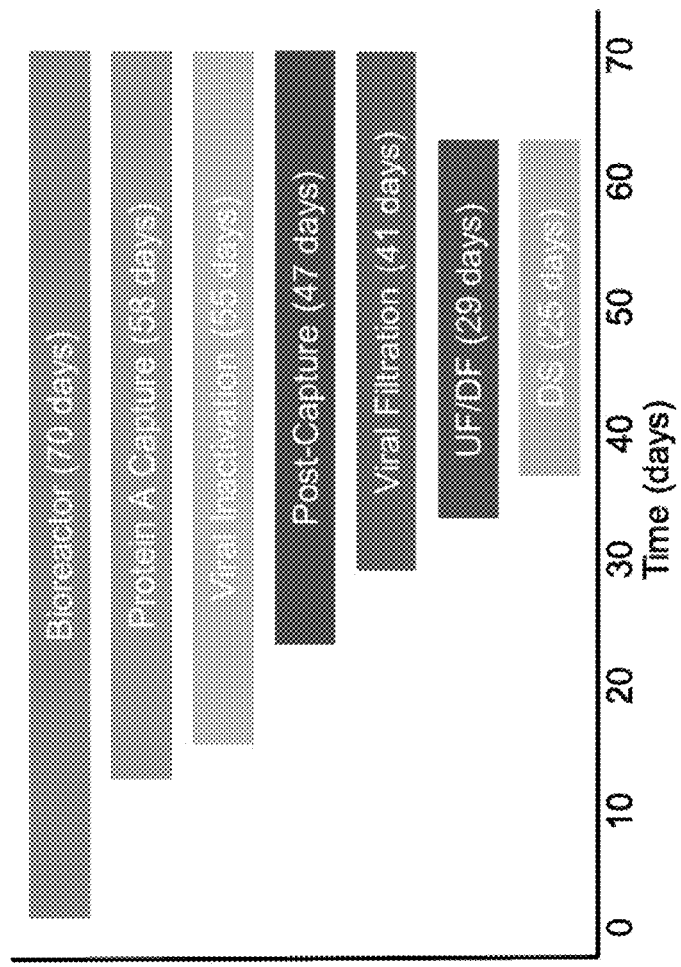
Figures 3A, 3B:
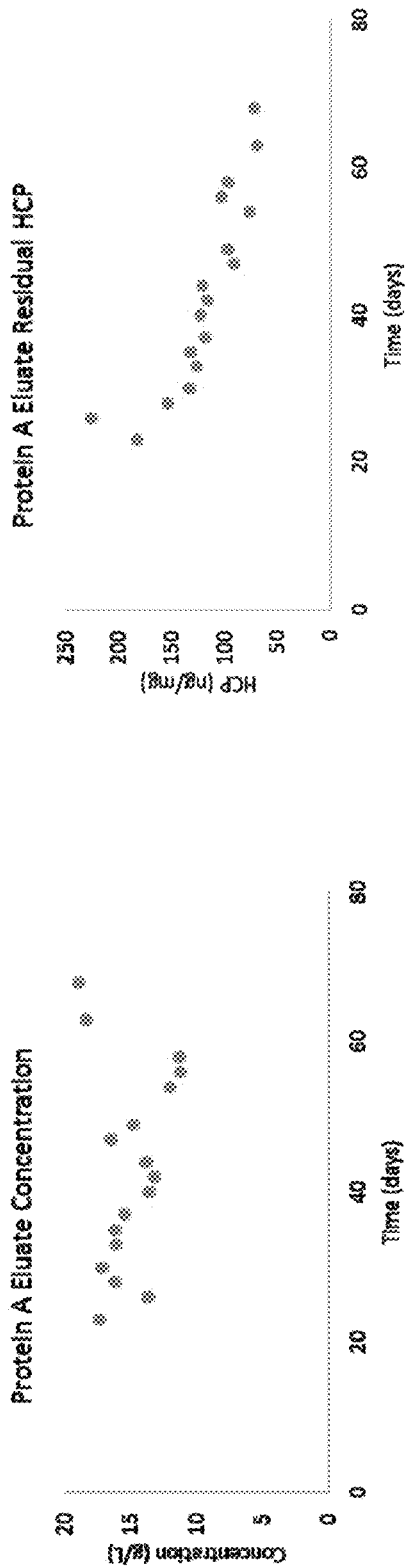
FIGS. 3A-3F are graphs showing Protein A operation performance for the methods and systems disclosed herein.
Figure 3D:
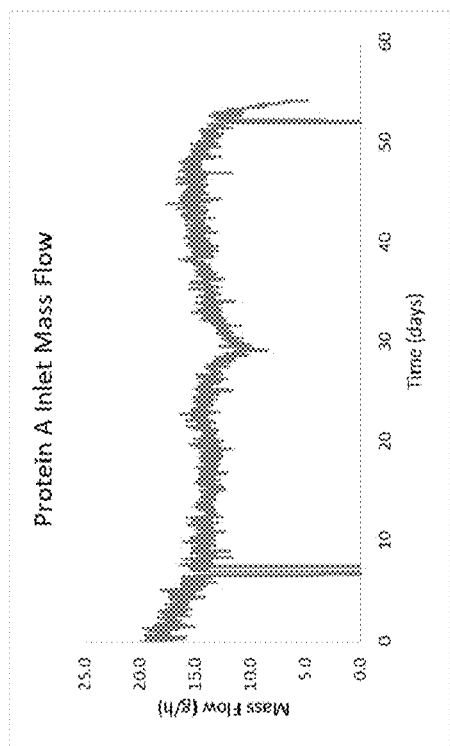
Figure 3C:
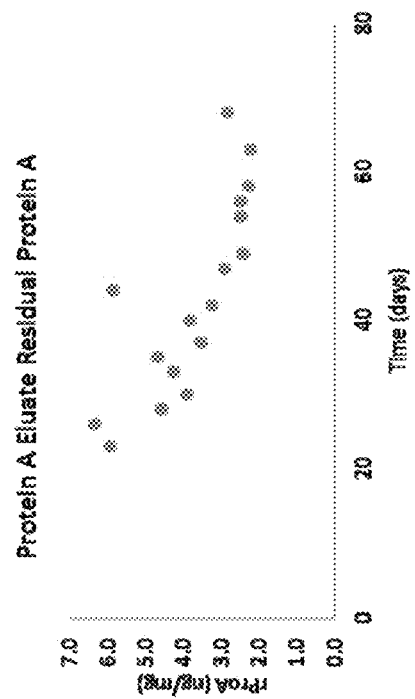
Figure 3F:
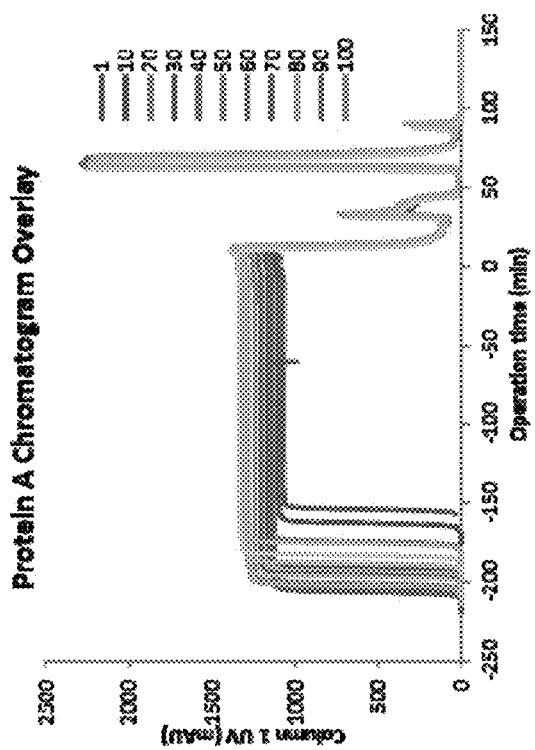
Figure 3E:
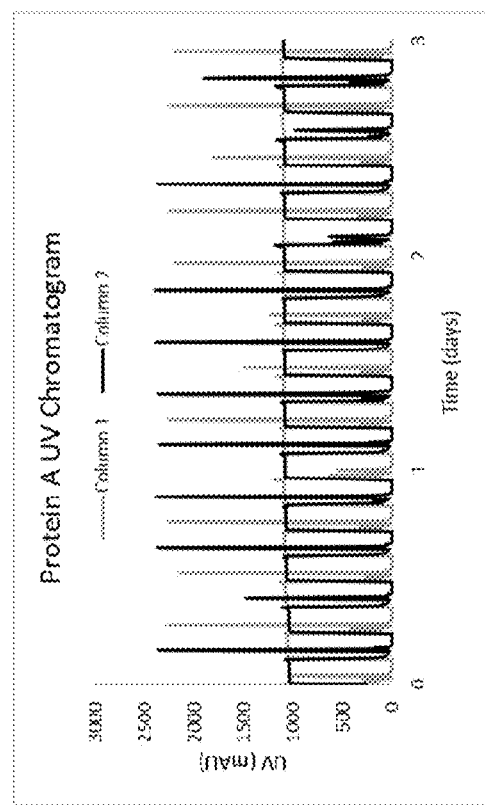
Figure 4B:
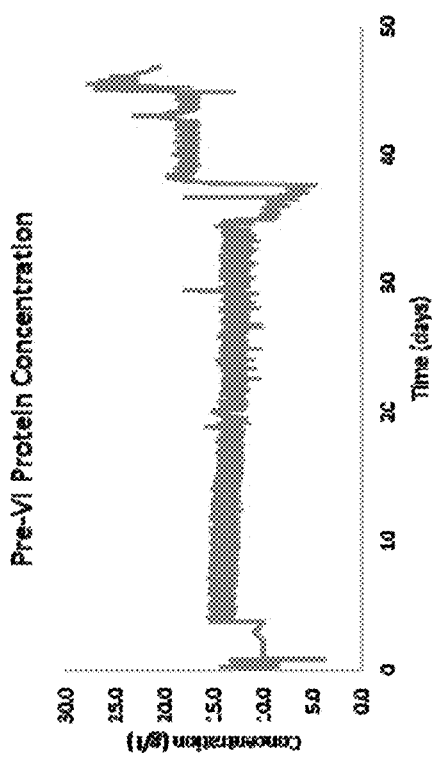
FIGS. 4A-4G are graphs showing viral inactivation operation performance for the methods and systems disclosed herein.
Figure 4A:
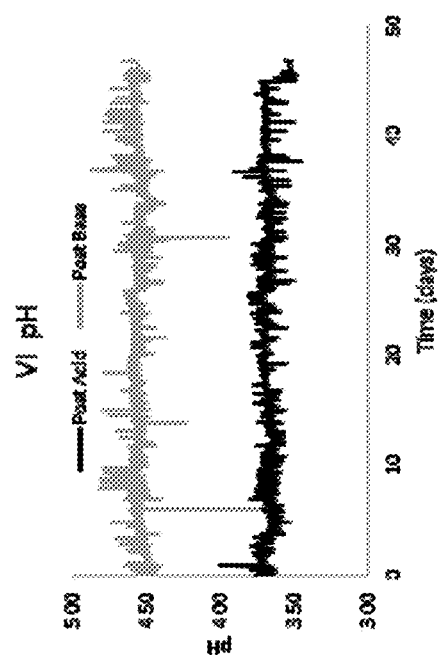
Figure 4D:
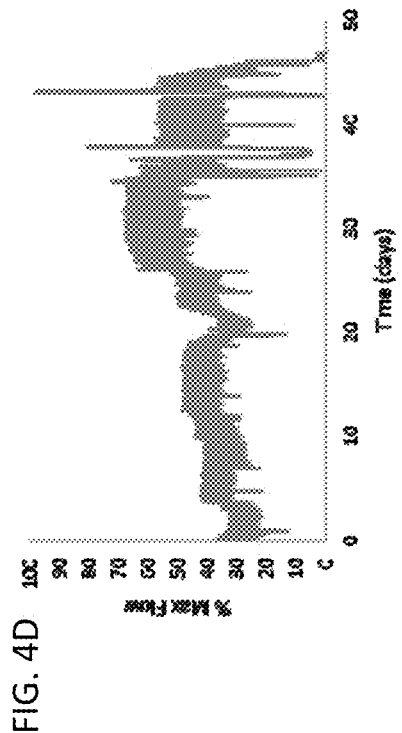
Figure 4C:
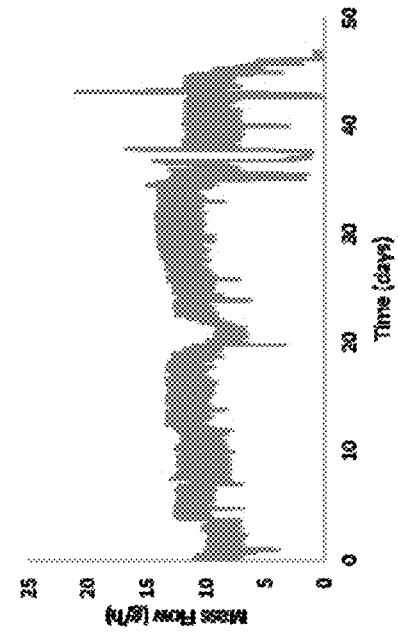
Figure 4E:
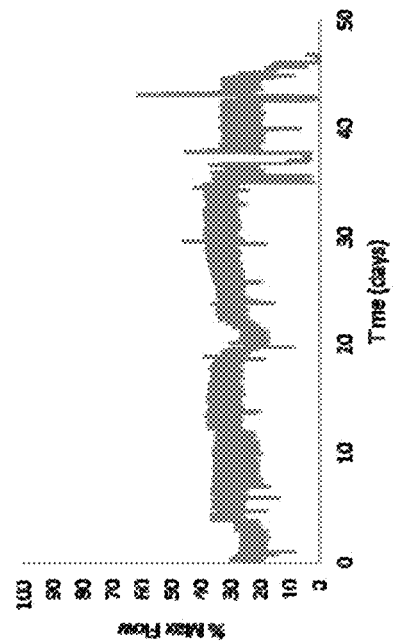
Figure 4G:
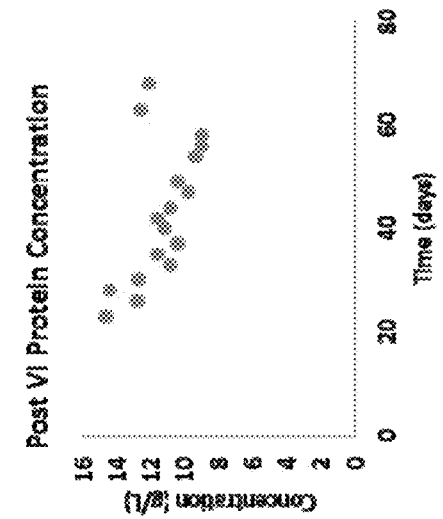
Figure 4F:
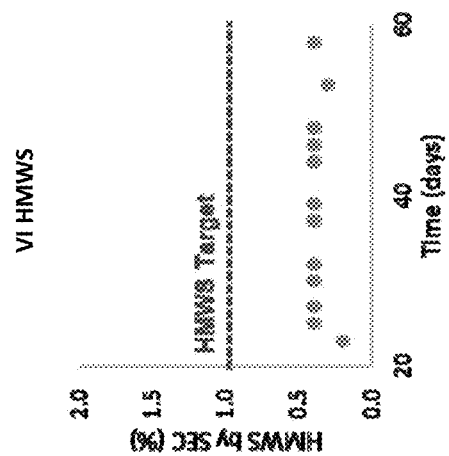
Figure 5B:
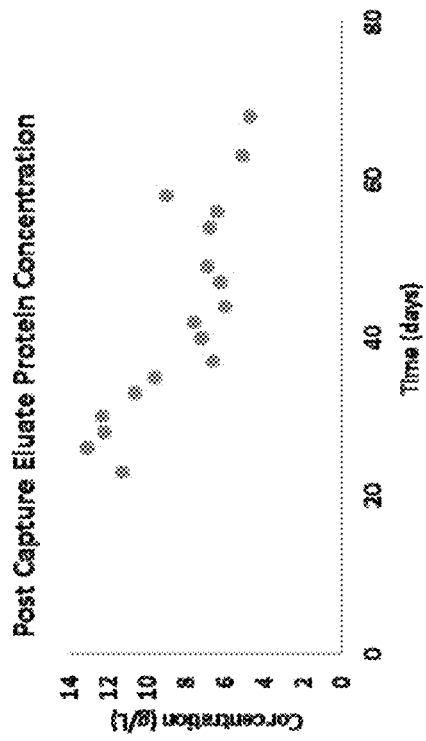
FIGS. 5A-5D are graphs showing post-capture operation performance for the methods and systems disclosed herein.
Figure 5A:
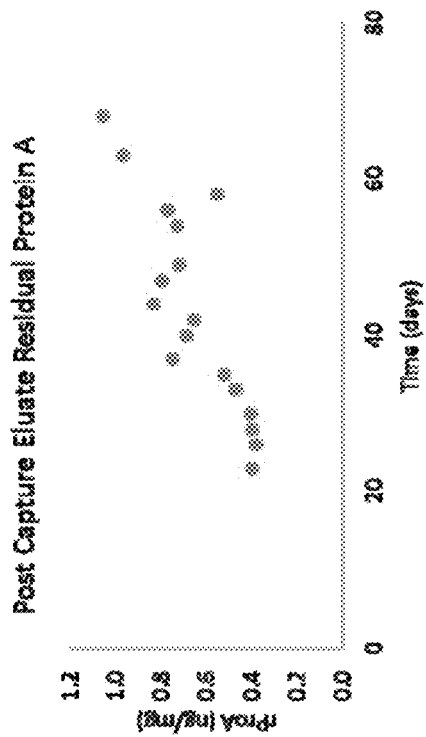
Figures 5C, 5D:
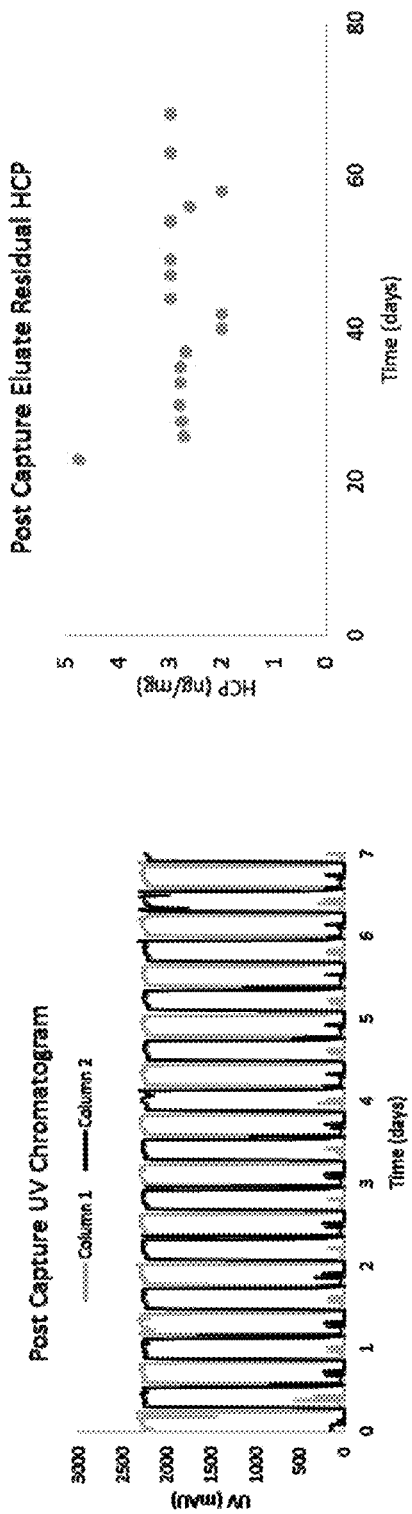

The present disclosure relates to methods and systems for the continuous production of recombinant proteins. In particular embodiments, the disclosure relates to methods and systems using capture chromatography, post-capture chromatography, and ultrafiltration/diafiltration for the production of recombinant proteins. The methods and systems described herein provide for the continuous and time-efficient production of a recombinant protein.

As utilized in accordance with the present disclosure, unless otherwise indicated, all technical and scientific terms shall be understood to have the same meaning as commonly understood by one of ordinary skill in the art. Unless otherwise required by context, singular terms shall include pluralities and plural terms shall include the singular.

In some embodiments provided herein is a continuous method for producing a recombinant protein, the method comprising capturing the recombinant protein from a substantially cell-free sample using one or a plurality of capture chromatography systems and eluting the recombinant protein from the one or plurality of capture chromatography systems to produce eluates comprising the recombinant protein, wherein the eluates are homogenized into a single mixture comprising the recombinant protein, subjecting the homogenized single mixture to one or a plurality of post-capture chromatography systems and collecting product output comprising the recombinant protein, and subjecting the product output to ultrafiltration and diafiltration to purify the recombinant protein, wherein the method is integrated and runs continuously.

Also provided herein is a manufacturing system for producing a recombinant protein, the manufacturing system comprising a first operation unit comprising a bioreactor comprising host cells that produce the recombinant protein, a second operation unit comprising one or a plurality of capture chromatography systems, a third operation unit comprising one or a plurality of post-capture chromatography systems, and a fourth operation unit comprising an ultrafiltration system and diafiltration system.

In some embodiments, the manufacturing system comprises a fifth operation unit located between the first operation unit and the second operation unit, wherein the fifth operation unit comprises a subsystem for preforming virus inactivation. In some embodiments, the manufacturing system comprises a sixth operation unit located between the third operation unit and the fourth operation unit, wherein the sixth operation unit comprises a second subsystem for preforming virus filtration. In some embodiments, the manufacturing system comprises a seventh unit operation comprising a third subsystem, wherein the third subsystem comprises in-line excipients for formulating a therapeutic drug substance.

"Substantially cell-free," as used herein, refers to a sample that is at least or about 90% free (e.g., at least or about 95%, 96%, 97%, 98%, or at least or about 99% free, or about 100% free) of a specified substance such as a mammalian cell.

In particular embodiments, the substantially cell-free sample is removed from a perfusion bioreactor comprising host cells that produce the recombinant protein, a fed-batch bioreactor comprising host cells that produce the recombinant protein, or a clarified liquid culture comprising host cells that produce the recombinant protein.

"Liquid culture medium," as used herein, refers to a fluid that contains sufficient nutrients to allow a cell to grow or proliferate in vitro. For example, a liquid culture medium can contain one or more of: amino acids (e.g., 20 amino acids), a purine (e.g., hypoxanthine), a pyrimidine (e.g., thymidine), choline, inositol, thiamine, folic acid, biotin, calcium, niacinamide, pyridoxine, riboflavin, thymidine, cyanocobalamin, pyruvate, lipoic acid, magnesium, glucose, sodium, potassium, iron, copper, zinc, and sodium bicarbonate. In some embodiments, a liquid culture medium can contain serum from a mammal. In some embodiments, a liquid culture medium does not contain serum or another extract from a mammal (a defined liquid culture medium). In some embodiments, a liquid culture medium can contain trace metals, a mammalian growth hormone, and/or a mammalian growth factor. Additional suitable liquid culture mediums are known in the art and are commercially available.

"Perfusion bioreactor," as used herein, refers to a bioreactor containing a plurality of cells in a first liquid culture medium, wherein the culturing of the cells present in the bioreactor includes periodic or continuous removal of the first liquid culture medium and at the same time or shortly thereafter adding substantially the same volume of a second liquid culture medium to the bioreactor. In some embodiments, there is an incremental change (e.g., increase or decrease) in the volume of the first liquid culture medium removed and added over incremental periods (e.g., an about 24-hour period, a period of between about 1 minute and about 24 hours, or a period of greater than 24 hours) during the culturing period (e.g., the culture medium refeed rate on a daily basis). The fraction of media removed and replaced each day can vary depending on the particular cells being cultured, the initial seeding density, and the cell density at a particular time.

"Fed-batch bioreactor," as used herein, refers to a bioreactor containing a plurality of cells in which necessary nutrients for cell growth and product formation are fed either intermittently or continuously by one or more feed streams.

"Clarified liquid culture medium," as used herein, refers to a liquid culture medium obtained from a bacterial or yeast cell culture that is substantially free (e.g., at least 80%, 85%, 90%, 92%, 94%, 96%, 98%, or 99% free) of bacteria or yeast cells.

"Recombinant protein," as used herein, refers to an immunoglobulin, protein fragment, engineered protein, blood factor, nanobody, or enzyme, including an antibody or antibody fragment therefore.

"Unit operation," as used herein, refers to a functional step that can be performed in a method of manufacturing a recombinant protein, or a component of a system used in a process of manufacturing a recombinant protein. For example, a unit of operation can be filtering (e.g., removal of contaminant bacteria, yeast viruses, or mycobacteria, and/or particular matter from a fluid containing a recombinant therapeutic protein), capturing, epitope tag removal, purifying, holding or storing, polishing, viral inactivating, adjusting the ionic concentration and/or pH of a fluid containing the recombinant protein, and removing unwanted salts.

The terms "continuous method" or "continuous system," as used herein, refer to a method or system which a fluid is continuously fed through at least a part of the unit operation. A unit operation is continuous if it is capable of processing a continuous flow input for prolonged periods of time. A continuous unit operation has minimal internal hold volume. The output can be continuous or discretized in small packets produced in a cyclic manner. A method is continuous if it is composed of integrated (physically connected) continuous unit operations with zero or minimal hold volume in between.

"Integrated method," as used herein, refers to a method which is performed using structural elements that function cooperatively to achieve a specific result (e.g., the generation of a recombinant protein from a liquid culture medium).

"Eluate," as used herein, refers to a fluid that is emitted from a chromatography column or chromatographic membrane that contains a detectable amount of a recombinant protein.

"Chromatography media," as used herein, refers to the material that is packed into a chromatography column.

In some embodiments, the system disclosed herein is a closed system. A closed system includes unit operations that are designed and operated to limit exposure to the outside environment. Materials may be introduced to a closed system, but the addition must be done in such a way to avoid exposure of the product to the room environment.

The methods and systems disclosed herein comprise capturing a recombinant protein using one or a plurality of capture chromatography systems and eluting the recombinant protein from the one or plurality of capture chromatography systems to produce eluates comprising the recombinant protein. The chromatography media contained in one or more of the capture chromatography systems can be a resin that utilizes a capture mechanism (e.g., Protein A-binding capture mechanism, Protein G-binding capture mechanism, antibody- or antibody fragment-binding capture mechanism, substrate-binding capture mechanism, cofactor-binding capture mechanism, tag-binding capture mechanism, and/or aptamer-binding capture mechanism). In some embodiments, the one or plurality of capture chromatography systems comprise chromatography media consisting of resin beads, porous membranes, or nanofibers. In some embodiments, the chromatography media is functionalized for affinity chromatography, cation exchange chromatography, anion exchange chromatography, hydrophobic interaction chromatography, or mixed-mode chromatography. In some embodiments, the affinity chromatography media is a Protein A-based resin.

In some embodiments, the one or plurality of capture chromatography systems is a periodic counter current chromatography system (PCCS). In some embodiments, the PCCS includes two chromatography columns or includes a modified AKTA system (GE Healthcare, Piscataway, NJ) capable of running up to, for example, four, five, six, seven, eight, or more than eight columns. In some embodiments, the PCCS utilizes a column-switching mechanism. The column-switching events can be triggered by the detection of a level of recombinant protein detected by UV absorbance corresponding to a certain level of recombinant protein in the fluid passing through the chromatography systems, a specific volume of liquid (e.g., buffer), or specific time elapsed.

In order to capture the recombinant protein using capture chromatography systems, one must perform the sequential chromatographic steps of loading, washing, eluting, and regenerating the capture chromatography systems.

In some embodiments, the eluates from the one or plurality of capture chromatography systems are homogenized into a single mixture comprising the recombinant protein. In some embodiments, the homogenized single mixture is subjected to one or a plurality of post-capture chromatography systems and the product output comprising the recombinant protein is collected. The post-capture chromatography systems are used to remove remaining trace or small amounts of contaminants or impurities from a fluid containing a recombinant protein that is close to a final desired purity. In some embodiments, the one or a plurality of post-capture chromatography systems comprises chromatography media consisting of resin beads, porous membranes, or nanofibers. In some embodiments, the chromatography media is functionalized for affinity chromatography, cation exchange chromatography, anion exchange chromatography, hydrophobic interaction chromatography, or mixed-mode chromatography. In some embodiments, the one or plurality of post-capture chromatography columns is a periodic counter current chromatography system (PCCS).

In order to post-capture the recombinant protein using the post-capture chromatography systems, one must perform the sequential chromatographic steps of loading, washing, eluting, and regenerating the post-capture chromatography systems.

In some embodiments, the methods and systems include ultrafiltration (UF) and/or diafiltration (DF) to further purify and concentrate the recombinant protein. UF/DF can increase the concentration of the recombinant protein as well as replace buffering salts with a particular formulation buffer. Ultrafiltration (UF) refers to a type of membrane filtration in which hydrostatic pressure forces a liquid against a semipermeable membrane. In some embodiments, UF is performed with Tangential Flow Filtration (TFF) including single TFF and high performance tangential flow filtration (HPTFF). Single pass tangential flow filtration (SPTFF) refers to any TFF system in which the conversion in a single pass through the module (permeate flow rate divided by inlet feed flow rate) is large enough that the system can be operated without a recycle (recirculation) loop for the retentate. SPTFF can be used for in-line concentration between other unit operations, for example, to reduce process volume prior to a chromatography or precipitation step. Zydney, *Biotechnol. Bioeng.* 113(3): 465-75 (2016).

"Diafiltration," as used herein, refers to a method that uses ultrafiltration membranes to remove, replace, or lower the concentrations of salts or buffering components from solutions containing proteins, such as antibodies, peptides, nucleic acids, and other biomolecules. Continuous diafiltration (also referred to as constant volume diafiltration) involves washing out the original buffer salts (or other low molecular weight species) in the retentate by adding water or a new buffer, such as a formulation buffer, to the retentate to form a formulation containing the recombinantly produced polypeptide. Typically, the new buffer is added at the same rate as filtrate is being generated such that the retentate volume and product concentration does not change appreciably during diafiltration. In particular embodiments, the diafiltration is performed using a single-pass diafiltration cassette.

In some embodiments, the homogenized single mixture is subjected to virus inactivation before being subjected to one or a plurality of post-capture chromatography systems. In some embodiments, the virus inactivation comprises solvent-detergent solution inactivation, heating inactivation, or acidic pH inactivation.

With solvent-detergent viral inactivation, procedures involve subjecting the sample comprising the recombinant protein to an organic solvent and a detergent. The solvent-detergent combination can be any solvent-detergent combination known in the art such as tri-n-butyl phosphate and Triton X-100™, Tween 80™ and Sodium cholate and others.

Viral inactivation through heat inactivation involves subjecting the sample comprising the recombinant protein to elevated temperatures. In some embodiments, the methods include heating the sample to a temperature of greater than or equal to 45° C., 46° C., 47° C., 48° C., and up to about greater than or equal to 49° C., 50° C., 51° C., and up. In some embodiments, the sample is heated to a temperature between 45° C. and 65° C.

The period of time during which the sample is heated can vary. For example, in some embodiments, the sample is heated to the target temperature for a time period of between 1 minute and 6 hours. In some embodiments, the sample is heated to the target temperature for a time period of between 10 and 180 minutes, between 20 and 180 minutes, between 20 and 60 minutes, or between 20 and 40 minutes.

In some embodiments, acidic pH inactivation is performed by adjusting the homogenized single mixture to a low pH in-line with one or more solutions and incubating the adjusted homogenized single mixture at the low pH for a period of time that results in a virus inactivation mixture.

The methods and systems disclosed herein include in-line monitoring, including detection of a level of recombinant protein detected by UV absorbance, detection of flow-rate, and/or detection of volume of liquid (e.g., buffer). Monitoring the recombinant protein concentration (e.g., monitoring performed by UV monitoring) can be determined by any tool capable of in-line measurement of product concentration with feedback control.

In some embodiments, the homogenized single mixture is exposed to a low pH for a period of time between 15 minutes to 2 hours. In particular embodiments, the low pH is a pH between 3 and 5. The choice of pH level depends on the stability profile of the recombinant protein and other buffer components. After viral inactivation, the pH of the antibody solution can be adjusted to a more neutral pH, for example, between 4.0 to 8.5 prior to continuing the method.

In some embodiments, viral inactivation is performed in a tubular flow reactor as described by Parker et al., Biotechnol. Bioeng. 115(3): 606-16 (2018). In some embodiments, the tubular flow reactor has a defined minimum residence time of at least 30 minutes.

In some embodiments, a virus removal step such as viral filtration is included following collection of the product output from the post-capture chromatography systems. The virus removal step is performed to remove small non-enveloped viruses which are more resistant to the viral inactivation treatment. In some embodiments, the virus filtration is performed in a pressurized loop wherein the pressurized loop comprises a pressure vessel, a virus removal filter, and a sterilizing filter. In some embodiments, the virus removal filter in the pressurized loop is a hollow fiber virus filter. In some embodiments, the pressure vessel is a single-use, closed, and sterilizable vessel. As used herein, the term "sterilizable" refers to a vessel formed from materials that are compatible with known sterilization methods. In some embodiments, the virus filtration is performed using dead-end filtration. As used herein, "dead-end filtration" refers to a filtration where the entire fluid stream being filtered goes through the filter with no recycle or retentate flow. In some embodiments, the virus removal filter is an ultrafilter or a nanofilter. An example of a suitable viral filtration system is disclosed in International Publication No. WO 2018/035116, which is incorporated by reference herein.

In some embodiments, the first unit operation comprises an outlet that is connected to an inlet on the second unit operation, wherein the second unit operation comprises an outlet that is connected to an inlet on the third unit operation, wherein the third unit operation comprises an outlet that is connected to an inlet on the fourth unit operation. In some embodiments, the first unit operation comprises an outlet that is connected to an inlet on the fifth unit operation, wherein the fifth unit operation comprises an outlet that is connected to an inlet on the second unit operation, wherein the second unit operation comprises an outlet that is connected to an inlet on the third unit operation, wherein the third unit operation comprises an outlet that is connected to an inlet on the sixth unit operation, wherein the sixth unit operation comprises an outlet that is connected to an inlet on the fourth unit operation.

In some embodiments, the systems disclosed herein include a surge vessel between each of the first unit operation, the second unit operation, the third unit operation, and the fourth unit operation. The surge vessel is capable of holding any liquid culture before moving into the next operation unit.

The systems described herein can also include a fluid conduit that is disposed between any of the unit operations. Suitable fluid conduits can be a tube that is made of polyethylene, polycarbonate, or plastic. The fluid conduits can also include one of more of the following in any combination: one or more in-line buffer adjustment reservoirs that are in fluid communication with the fluid conduit and are positioned such that the buffer stored within the in-line buffer adjustment reservoir(s) is added to the fluid present in the fluid conduit; and one or more filters that are disposed in the fluid conduit such that they are capable of filtering (e.g., removing bacteria) the fluid present in the fluid conduit.

In some embodiments, the systems provided herein include a pump system. A pump system can include one or more the following: one or more pumps as known in the art, one or more filters known in the art, and one or more UV detectors.

In some embodiments, following ultrafiltration/diafiltration, one or more excipients are added to the product output to generate a therapeutic drug substance.

"Therapeutic drug substance," as used herein, refers to a substance including a recombinant protein that has been sufficiently purified or isolated from contaminating proteins, lipids, and nucleic acids (e.g., contaminating proteins, lipids, and nucleic acids present in a liquid culture medium or from a host cell (e.g., from a mammalian, yeast, or bacterial host cell) and biological contaminants (e.g., viral and bacterial contaminants), and can be formulated into a pharmaceutical agent without any further substantial purification and/or decontamination step.

In some embodiments, the system disclosed herein is on a skid. "Skid," as used herein, refers to a three-dimensional solid structure that can act as a platform or support for a system described herein. A skid can, if it comprises one or more structures that enable movement (e.g., wheels, rollers, or the like), confer mobility on the system or a portion thereof.

In some embodiments, the methods and systems have a recovery of the recombinant protein of at least about 40%, 50%, 55%, or 60%, and up to about 65%, 70%, 75%, 80%, 85%, 90%, or 95%. In some embodiments, the purification recovery is at least about 60% to about 70%.

In some embodiments, the methods and systems described herein result in a net yield of recombinant protein in the therapeutic protein drug substance of at least about 5 g/day, 10 g/day or 20 g/day, 30 g/day or 40 g/day, and up to about at least about 200 g/day, 300 g/day, 400 g/day, 500 g/day, or 1000 g/day over a continuous period of at least about 5 days, 10 days, 20 days, or 30 days, and up to about at least about 280 days, 290 days, 300 days, 310 days, 320 days, 330 days, 340 days, 350 days, or 365 days.

EXAMPLES

The Examples that follow are illustrative of specific embodiments of the disclosure, and various uses thereof. They are set forth for explanatory purposes only and should not be construed as limiting the scope of the disclosure in any way.

Example 1: Continuous Production of Recombinant Protein

A 100-L intensified perfusion bioreactor coupled with dual ATFs was used to produce a recombinant monoclonal antibody (mAb) over the course of 70 days. The cell-free mAb-containing media (harvest) was continually pumped to a 100-L harvest surge vessel for further processing.

The antibody containing media was captured using 2×1-L (8×20 cm) pre-packed and irradiated Protein A affinity chromatography columns operated in bind-and-elute MCC mode on a pilot scale steam-in-place PCC skid. The capture step was executed such that one of the two columns was always being loaded from the harvest surge vessel and that the average inlet volumetric flowrate to the capture step matched the average outlet volumetric flowrate from the perfusion bioreactor. Loading on the Protein A columns was controlled by Delta UV to approximately 3% breakthrough. Individual capture column eluates were collected in a 5-L mixing vessel prior to viral inactivation. The Protein A operation was integrated with the perfusion bioreactor on day 12 and ran continuously for 58 days. Data summarizing Protein A operation performance are shown in FIGS. 3A-3F.

The individual Protein A eluates were mixed in the 5-L mixing vessel to ensure a homogeneous stream for the virus inactivation unit operation. The outflow of the mixing vessel was automated such that the entire vessel would be processed before the next Protein A elution cycle. The homogenized Protein A eluate was adjusted in-line by addition of 1 M acetic acid to a target pH of 3.6. The low pH adjusted Protein A eluate was then pumped through a tubular flow reactor (TFR) with a defined minimum residence time of ≥30 minutes to ensure sufficient time at low pH to achieve complete viral inactivation. The virus inactivated Protein A eluate was then adjusted in-line by addition of 0.75 M sodium acetate to a target pH of 4.5. The adjusted virus inactivated Protein A eluate was then processed through a sterilizing grade filter and continuously collected in a small surge vessel for further processing. The virus inactivation operation was integrated with the preceding operations on day 15, and ran continuously for 55 days. Data summarizing viral inactivation operation performance are shown in FIGS. 4A-4G.

The adjusted virus inactivated Protein A eluate was further processed through two orthogonal chromatography operations using mixed-mode anion exchange resin and hydrophobic interaction chromatography resin, operated in flow-through mode. For this example process, there was no interstep adjustment between the two post-capture chromatography operations, allowing the flowthrough from the mixed-mode column to be directly loaded on to the hydrophobic interaction column. The post capture train consisted of 2×0.2 L (5×10 cm) pre-packed mixed-mode columns and 2×0.2 L (5×10 cm) pre-packed hydrophobic interaction columns, operated in MCC mode on the same PCC skid as the Protein A operation. The adjusted and virus inactivated Protein A eluate stream was continuously loaded on one of the two parallel post-capture trains with column loading automated such that mass equivalent to approximately 2 Protein A eluates was loaded in each post-capture cycle.

The combined mixed-mode/hydrophobic interaction flowthrough (labeled as post capture eluate) was continuously collected in a small surge vessel for further processing. The post-capture chromatography operation was integrated with the preceding unit operations on Day 23, and ran continuously for 47 days. Data summarizing the post-capture chromatography operation performance are shown in FIGS. 5A-5D.

Figure 6A:
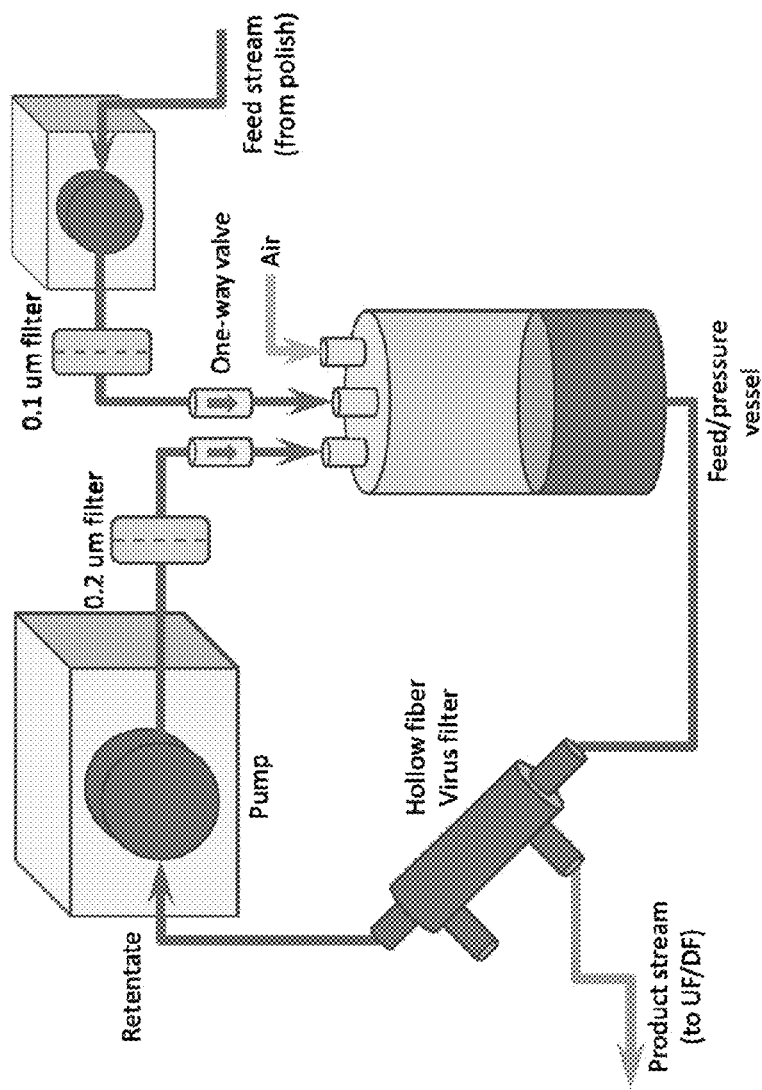
FIG. 6A shows a schematic of the virus filtration for the methods and systems disclosed herein.
Figure 6C:
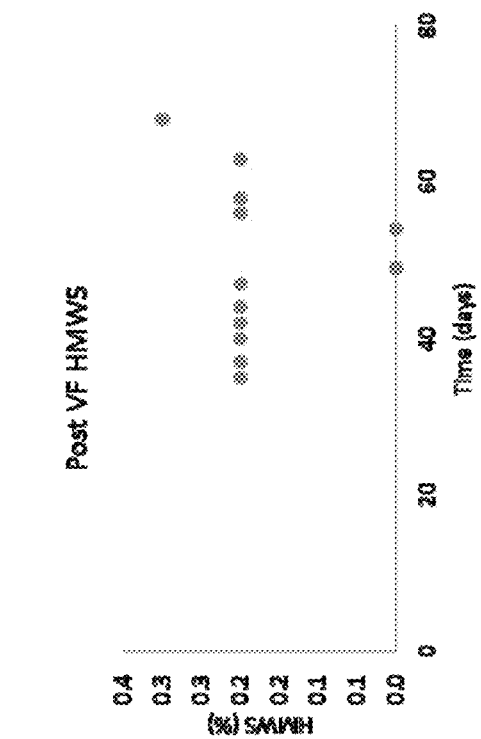
FIGS. 6B-6G are graphs showing viral filtration operation performance for the methods and systems disclosed herein.
Figure 6B:
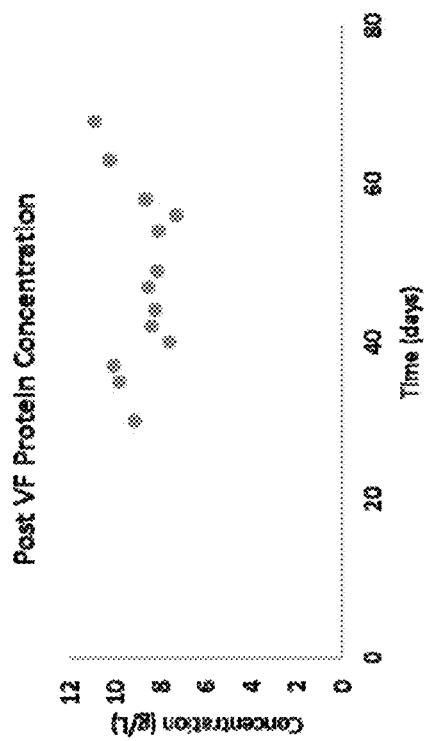
Figure 6E:
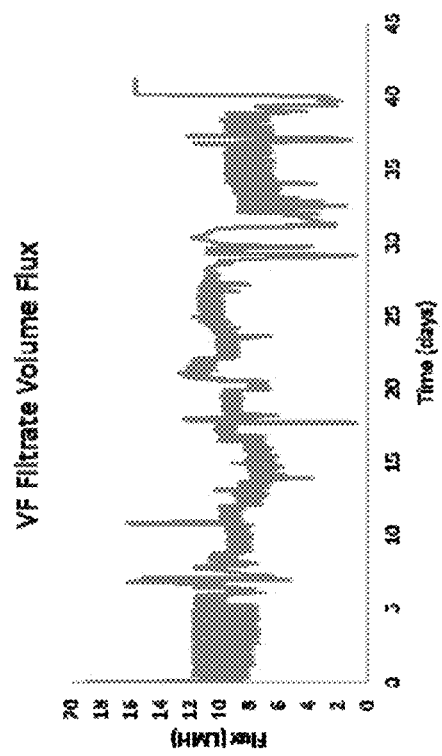
Figure 6D:
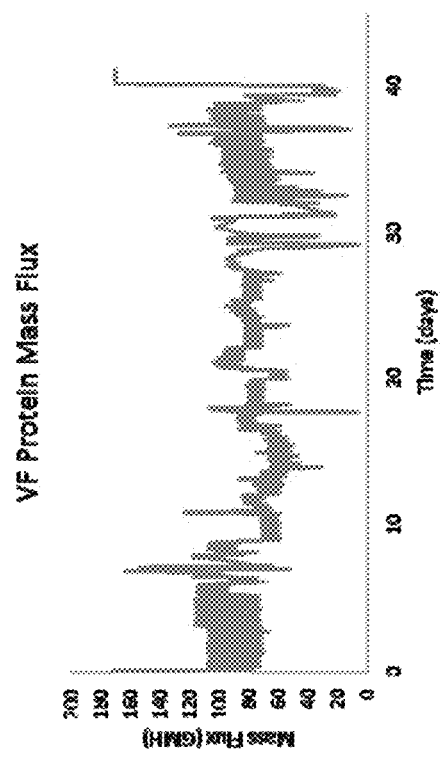
Figure 6G:
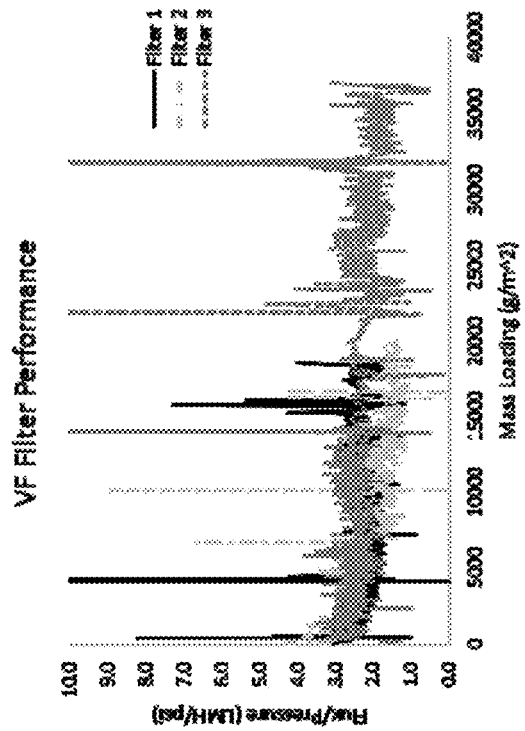
Figure 6F:
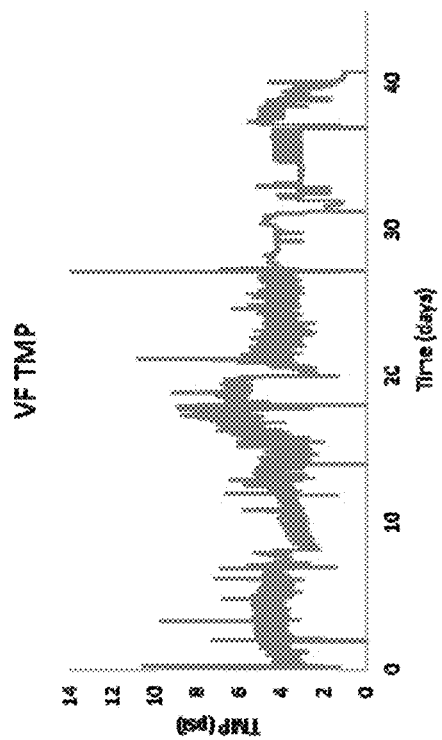
Figure 7B:
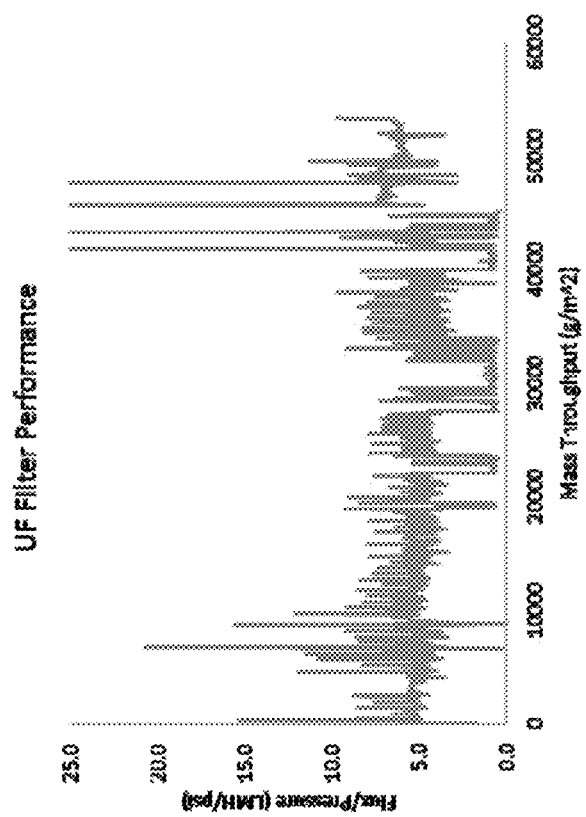
FIGS. 7A-7E are graphs showing ultrafiltration operation performance for the methods and systems disclosed herein.
Figure 7A:
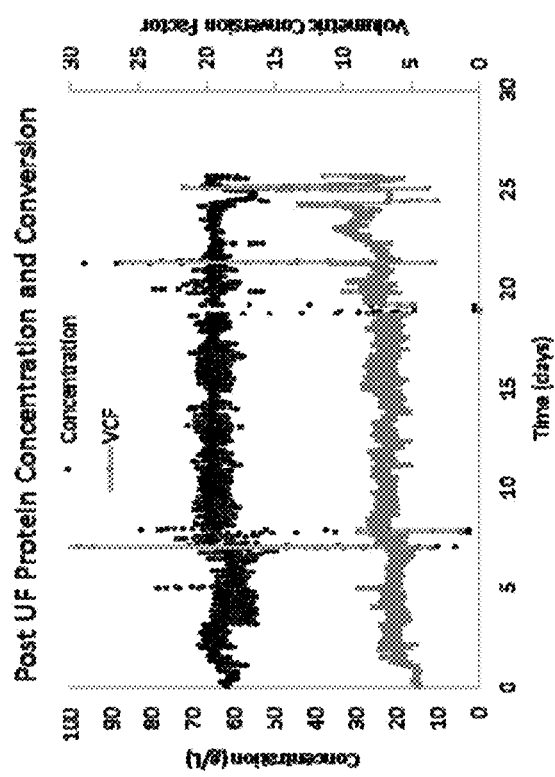
Figure 7C:
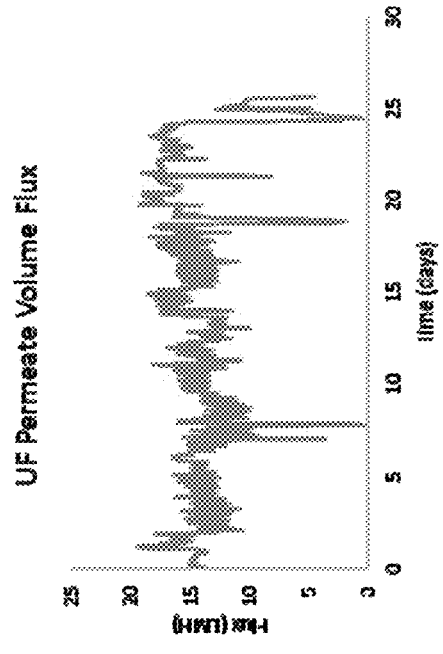
Figure 7D:
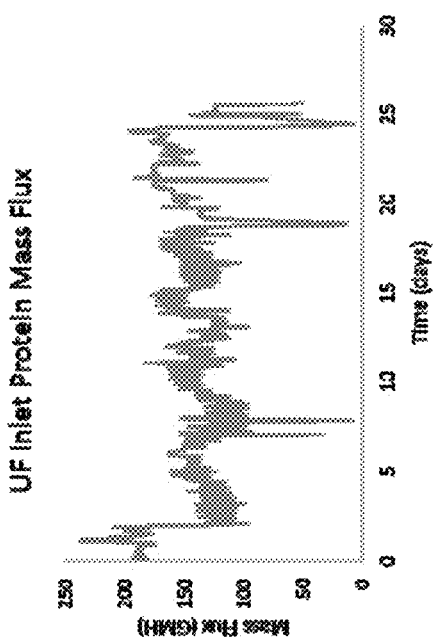
Figure 7E:
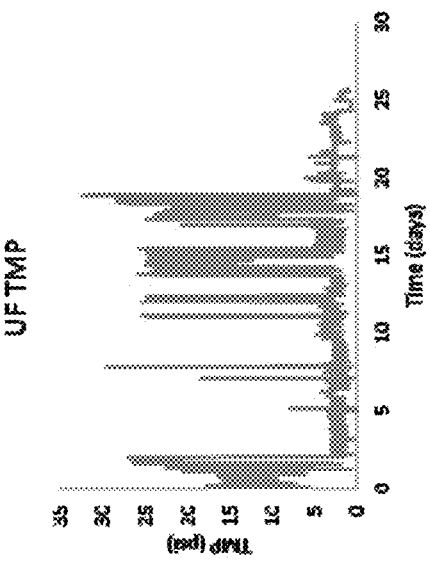
Figure 8B:
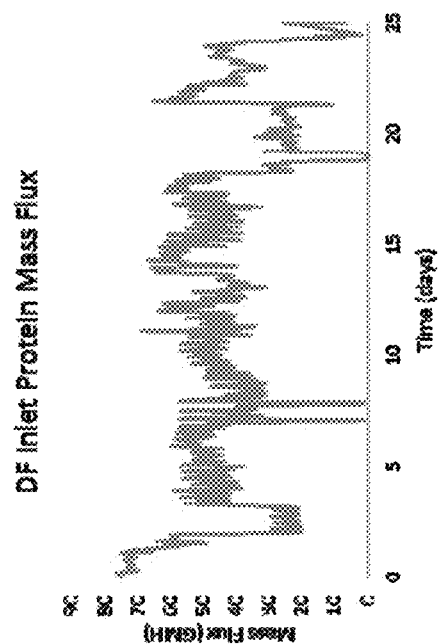
FIGS. 8A-8E are graphs showing diafiltration operation performance for the methods and systems disclosed herein.
Figure 8A:
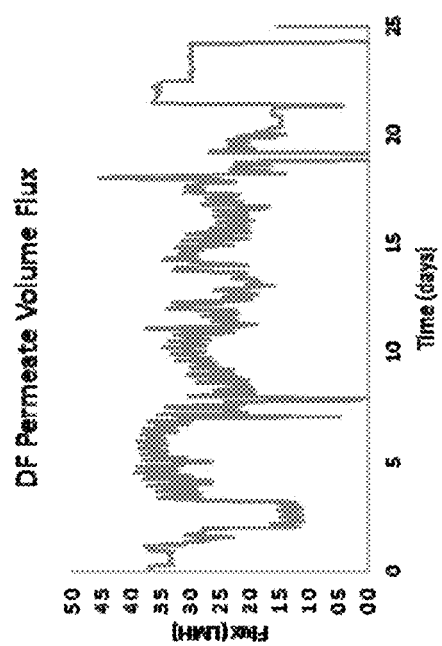
Figure 8D:
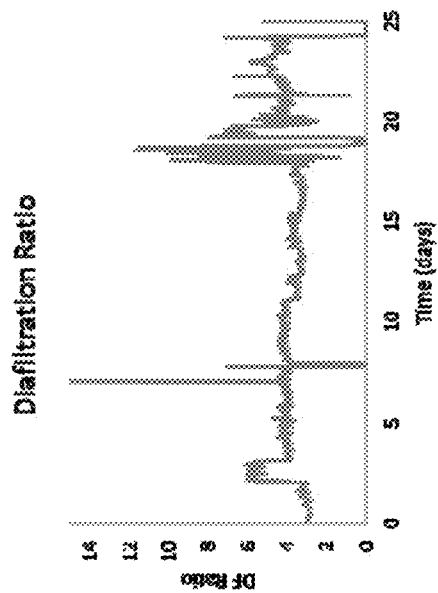
Figure 8C:
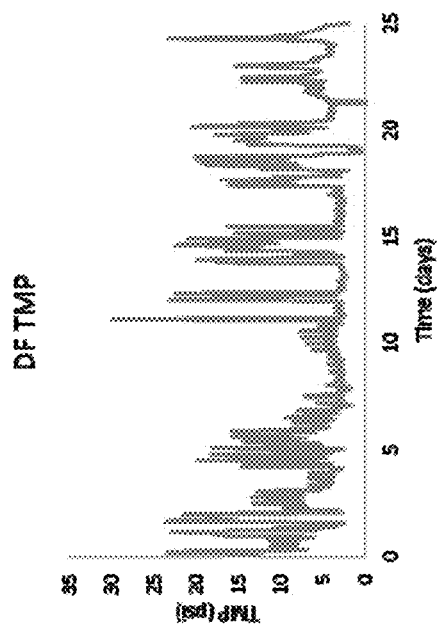
Figure 8E:
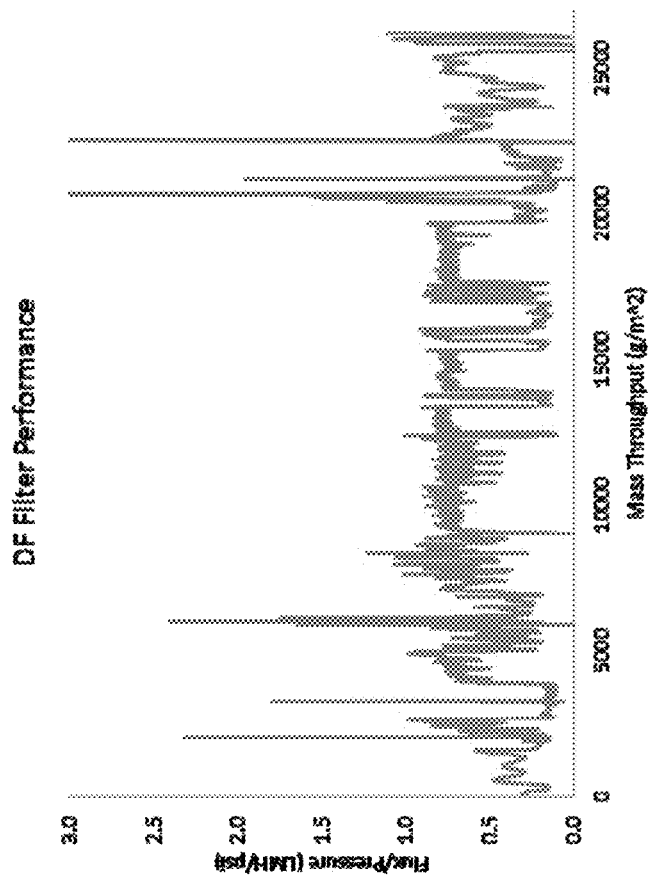
Figures 9A, 9B:
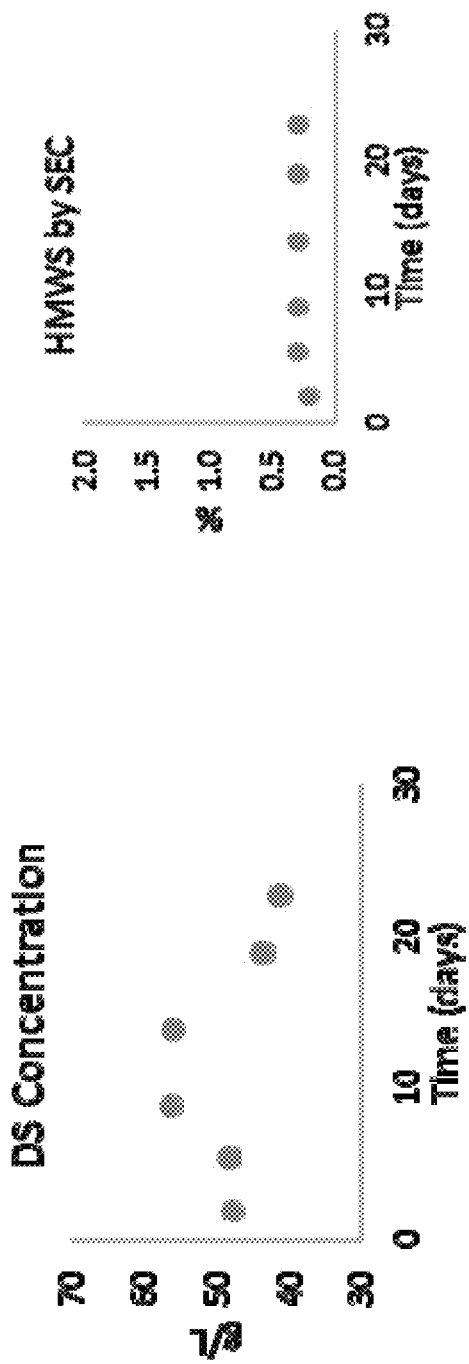
FIGS. 9A-9H are graphs showing attributes for a drug substance produced using the methods and systems disclosed herein.
Figure 9D:
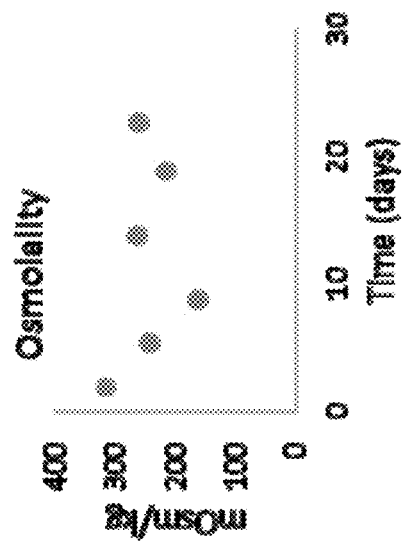
Figure 9C:
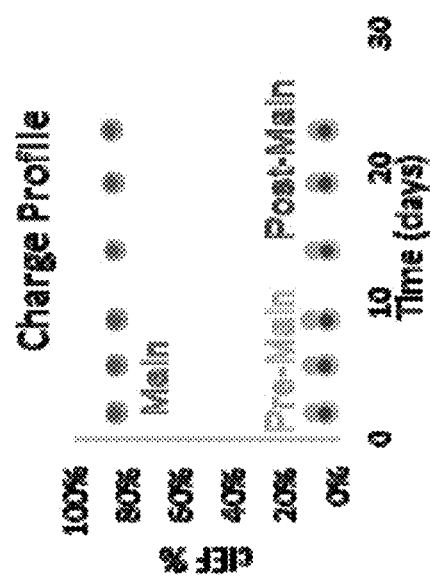
Figure 9F:
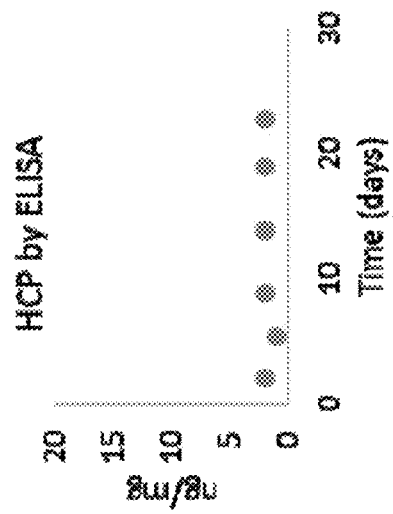
Figure 9E:
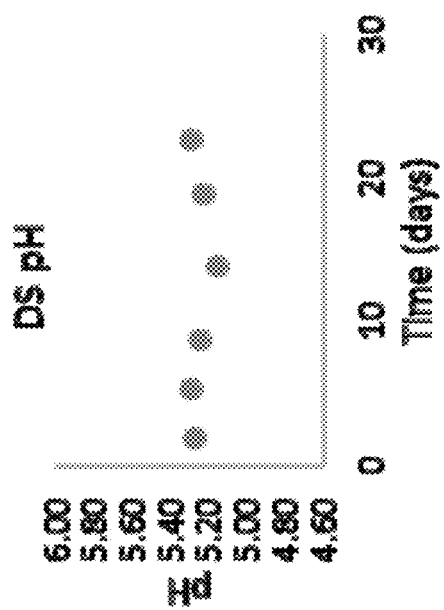
Figure 9H:
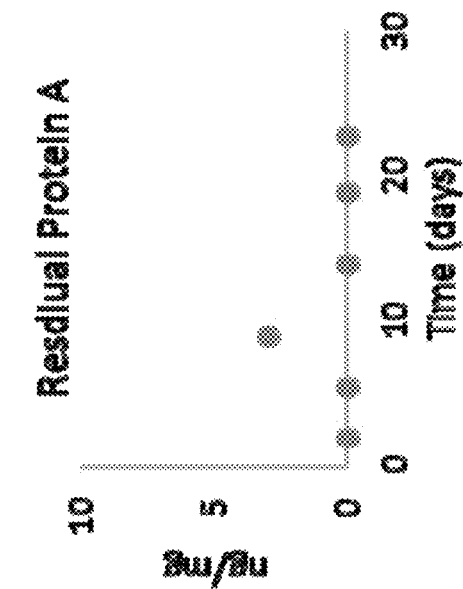
Figure 9G:
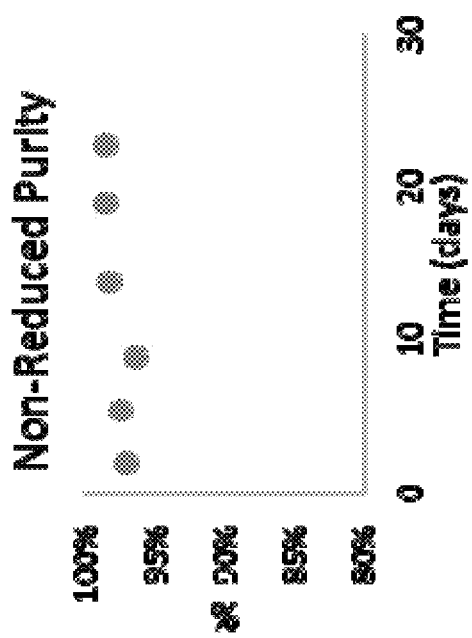

The post-capture eluates were further processed through a 0.1 m$^2$ Planova 20N (AK Bio) virus removal filter operated in tangential flow mode. Post-capture eluate was continuously transferred from the surge vessel to a pressurized loop containing a pressure vessel, the virus removal filter, a sterilizing grade filter, and a peristaltic pump to drive the recirculation, as shown in FIG. 6A. The pressure in the loop was automated so the net volumetric flowrate through the virus filter (permeate flux) was equal to the net volumetric flowrate out from the post-capture operation. The Planova 20N filter was periodically replaced based on preliminary virus validation studies. The virus filtered material was continuously collected in a small surge vessel for further processing. The virus filtration operation was integrated with the preceding unit operations on Day 29, and ran continuously for 41 days. Data summarizing viral filtration operation performance are shown in FIGS. 6B-6F.

The virus filtered material was further processed via ultrafiltration using a 0.065 m$^2$ ILC single-pass TFF (SP-TFF) cassette and concentrated to a target mAb concentration of 65 g/L. Material was pumped from the post virus filtration surge vessel to the inlet of the SP-TFF cassette at a volumetric flowrate that matched the outlet flowrate from the virus filtration operation. The retentate flowrate from the SP-TFF cassette was automatically controlled using a feedback loop via an in-line measurement of the product concentration to maintain the target concentration value. The concentrated mAb stream was then pumped directly to the inlet of a single-pass diafiltration (SP-DF) cassette to perform in-line buffer exchange. Diafiltration buffer was pumped to the buffer inlet of the SP-DF cassette and buffer flow was automated to maintain a constant ratio of buffer to product flow. The retentate flowrate was controlled to match the inlet flowrate. The buffer exchanged DF retentate stream was then formulated by the in-line addition of a concentrated excipient solution to generate formulated bulk. The formulated bulk was further processed through a sterilizing grade filter to generate drug substance, which was collected in a single-use vessel. The ultrafiltration and diafiltration operations were integrated with the preceding unit operations on Day 42, and ran continuously for 29 days. The formulation operation and drug substance generation was integrated on Day 46, and ran continuously for 25 days. Over the course of 25 days, 6 batches of drug substance were generated. Data summarizing ultrafiltration and diafiltration operation performance are shown in FIGS. 7A-7E and FIGS. 8A-8D. FIGS. 9A-9H show attributes for the generated drug substance.

Example 2: Continuous Production of Recombinant Protein

A 100-L intensified perfusion bioreactor coupled with dual ATFs was used to produce a recombinant monoclonal antibody (mAb) over the course of 27 days. The cell-free mAb-containing media (harvest) was continually pumped to a 100-L harvest surge vessel for further processing.

The antibody containing media was captured using 2×1-L (8×20 cm) pre-packed and irradiated Protein A affinity chromatography columns operated in bind-and-elute MCC mode on a pilot scale steam-in-place PCC skid. The capture step was executed such that one of the two columns was always being loaded from the harvest surge vessel and that the average inlet volumetric flowrate to the capture step matched the average outlet volumetric flowrate from the perfusion bioreactor. Loading on the Protein A columns was controlled by Delta UV to approximately 3% breakthrough. Individual capture column eluates were collected in a 5-L mixing vessel prior to viral inactivation. The Protein A operation was integrated with the perfusion bioreactor on day 12 and ran continuously for 15 days.

The individual Protein A eluates were mixed in the 5-L mixing vessel to ensure a homogeneous stream for the virus inactivation unit operation. The outflow of the mixing vessel was automated such that the entire vessel would be processed before the next Protein A elution cycle. The homogenized Protein A eluate was adjusted in-line by addition of 1 M acetic acid to a target pH of 3.6. The low pH adjusted Protein A eluate was then pumped through a 3D-printed, gamma irradiated tubular flow reactor (TFR) with a defined minimum residence time of ≥30 minutes to ensure sufficient time at low pH to achieve complete viral inactivation. The virus inactivated Protein A eluate was then adjusted in-line by addition of 0.75 M sodium acetate to a target pH of 4.5. The adjusted virus inactivated Protein A eluate was then processed through a sterilizing grade filter and continuously collected in a small surge vessel for further processing. The virus inactivation operation was integrated with the preceding operations on day 13, and ran continuously for 14 days.

The adjusted virus inactivated Protein A eluate was further processed through two orthogonal chromatography operations using mixed-mode anion exchange resin and hydrophobic interaction chromatography resin, operated in flow-through mode. The post capture train consisted of 2×0.2 L (5×10 cm) pre-packed and gamma-irradiated mixed-mode columns and 2×0.2 L (5×10 cm) pre-packed and gamma-irradiated hydrophobic interaction columns, operated in MCC mode. The adjusted and virus inactivated Protein A eluate stream was continuously loaded on one of the two mixed-mode columns and the flowthrough of the mixed-mode column was continuously loaded on one of the two hydrophobic interaction columns. The mixed-mode and hydrophobic interaction columns were independently loaded to their respective loading capacities.

The post-capture chromatography operation was integrated with the preceding unit operations on Day 14, and ran continuously for 13 days.

The post-capture eluates were further processed through a 0.1 m$^2$ Planova 20N (AK Bio) virus removal filter operated in tangential flow mode. Post-capture eluate was continuously transferred from the outlet of the hydrophobic interaction column to a pressurized loop containing a pressure vessel, the virus removal filter, a sterilizing grade filter, and a peristaltic pump to drive the recirculation. The pressure in the loop was automated so the net volumetric flowrate through the virus filter (permeate flux) was equal to the net volumetric flowrate out from the post-capture operation. The virus filtered material was continuously collected in a small surge vessel for further processing. The virus filtration operation was integrated with the preceding unit operations on Day 14, and ran continuously for 13 days.

The virus filtered material was further processed via ultrafiltration using 2×0.1 m$^2$ gamma-irradiated TFF capsules in series, operated in single-pass mode. The virus filtered material was concentrated to a target mAb concentration of 110 g/L. Material was pumped from the post virus filtration surge vessel to the inlet of the TFF capsule at a volumetric flowrate that matched the outlet flowrate from the virus filtration operation. The retentate flowrate from the TFF capsule was automatically controlled using a feedback loop via an in-line measurement of the product concentration to maintain the target concentration value. The concentrated mAb stream was then pumped directly to the inlet of a gamma-irradiated single-pass diafiltration (SP-DF) cassette to perform in-line buffer exchange. Diafiltration buffer was pumped to the buffer inlet of the SP-DF cassette and buffer flow was automated to maintain a constant ratio of buffer to product flow. The retentate flowrate was controlled to match the inlet flowrate. The buffer exchanged DF retentate stream was then formulated by the in-line addition of a concentrated excipient solution to generate formulated bulk. The addition of the formulation buffer was controlled via a feedback loop and an in-line sensor measuring the level of excipients in the formulated stream. The formulated bulk was further processed through a sterilizing grade filter to generate drug substance, which was collected in a single-use vessel. The ultrafiltration and diafiltration operation was integrated with the proceeding unit operations on Day 18 and the formulation operation was integrated on Day 20.

Due to issues with the in-line sensors, the UF/DF and formulation operations did not achieve steady state prior to the end of the campaign.

While the disclosure has been described in terms of various embodiments, it is understood that variations and modifications will occur to those skilled in the art. Therefore, it is intended that the appended claims cover all such equivalent variations that come within the scope of the disclosure as claimed. In addition, the section headings used herein are for organizational purposes only and are not to be construed as limiting the subject matter described.

Each embodiment herein described may be combined with any other embodiment or embodiments unless clearly indicated to the contrary. In particular, any feature or embodiment indicated as being preferred or advantageous may be combined with any other feature or features or embodiment or embodiments indicated as being preferred or advantageous, unless clearly indicated to the contrary.

All references cited in this application are expressly incorporated by reference herein.

What is claimed is:

1. A continuous method for producing a recombinant protein, the method comprising:
    (a) capturing the recombinant protein from a substantially cell-free sample using one or a plurality of capture chromatography systems and eluting the recombinant protein from the one or plurality of capture chromatography systems to produce eluates comprising the recombinant protein, wherein the eluates are homogenized into a single mixture comprising the recombinant protein;
    (b) subjecting the homogenized single mixture to one or a plurality of post-capture chromatography systems and collecting product output comprising the recombinant protein; and
    (c) subjecting the product output to ultrafiltration and diafiltration to purify the recombinant protein;
    wherein each step is performed by a unit operation, wherein each unit operation is physically connected from step (a) to step (c), and wherein the connected unit operations from step (a) to step (c) process a continuous flow comprising the recombinant protein from step (a) to step (c).

2. The method of claim 1 further comprising subjecting the homogenized single mixture to virus inactivation following step (a).

3. The method of claim 2, wherein virus inactivation comprises solvent-detergent solution inactivation, heat inactivation, or acidic pH inactivation.

4. The method of claim 3, wherein the acidic pH inactivation comprise:
    (a) adjusting the homogenized single mixture to a low pH in-line by adding one or more solutions; and
    (b) incubating the adjusted homogenized single mixture at the low pH for a period of time that results in a virus inactivation mixture.

5. The method of claim 4, wherein the period of time is between 15 minutes to 2 hours.

6. The method of claim 1 further comprising subjecting the product output of step (b) to virus filtration.

7. The method of claim 1, wherein the substantially cell-free sample is removed from a perfusion bioreactor comprising host cells that produce the recombinant protein, a fedbatch bioreactor comprising host cells that produce the recombinant protein, or a clarified liquid culture comprising host cells that produce the recombinant protein.

8. The method of claim 1, wherein the one or plurality of capture chromatography systems and the one or a plurality of post-capture chromatography systems comprises chromatography media comprising resin beads, porous membranes, or nanofibers.

9. The method of claim 8, wherein the chromatography media is functionalized for affinity chromatography, cation exchange chromatography, anion exchange chromatography, hydrophobic interaction chromatography, or mixed-mode chromatography.

10. The method of claim 9, wherein the affinity chromatography media is a Protein A-based resin.

11. The method of claim 1, wherein the one or plurality of capture chromatography systems and the one or a plurality of post-capture chromatography systems is a periodic counter current chromatography system (PCCS).

12. The method of claim 4, wherein incubating the adjusted homogenized single mixture at the low pH for a period of time that results in virus inactivation is performed in a tubular flow reactor.

13. The method of claim 4, wherein the addition of the one or more solutions is based on in-line recombinant protein concentration measurements and in-line flow-rate measurements.

14. The method of claim 6, wherein the virus filtration is performed in a pressurized loop.

15. The method of claim 14, wherein the pressurized loop comprises a pressure vessel, a virus removal filter, and a sterilizing filter.

16. The method of claim 15, wherein the pressure vessel is a single-use, closed, and sterilizable vessel.

17. The method of claim 16, wherein the virus removal filter is an ultrafilter or a nanofilter.

18. The method of claim 6, wherein the virus filtration is performed using dead-end filtration.

19. The method of claim 18, wherein the dead-end filtration is performed using an ultrafilter or a nanofilter.

20. The method of claim 1, wherein the ultrafiltration is performed with single pass tangential flow filtration.

21. The method of claim 1, wherein the diafiltration is performed using a single-pass diafiltration cassette.

22. The method of claim 1, wherein the recombinant protein is an antibody or antigen binding fragment thereof.

23. The method of claim 1 further comprising adding one or more excipients following step (c) to generate a therapeutic drug substance.

24. The method of claim 1, wherein the recombinant protein is purified using ultrafiltration by single pass tangential flow filtration and using single-pass diafiltration.

* * * * *

UNITED STATES PATENT AND TRADEMARK OFFICE
CERTIFICATE OF CORRECTION

| | | |
|---|---|---|
| PATENT NO. | : 11,912,741 B2 | Page 1 of 1 |
| APPLICATION NO. | : 16/837126 | |
| DATED | : February 27, 2024 | |
| INVENTOR(S) | : Coolbaugh et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 594 days.

Signed and Sealed this
Twelfth Day of August, 2025

Coke Morgan Stewart
*Acting Director of the United States Patent and Trademark Office*